(12) United States Patent
Sharpless et al.

(10) Patent No.: US 6,404,845 B1
(45) Date of Patent: Jun. 11, 2002

(54) AEROSTATIC ROTOR BEARING

(75) Inventors: Ronald Bryan Sharpless, Cleveland; William Charles Brunnett, Concord, both of OH (US)

(73) Assignee: Philips Medical Systems (Cleveland), Inc., Highland Heights, OH (US)

( * ) Notice: Subject to any disclaimer, the term of this patent is extended or adjusted under 35 U.S.C. 154(b) by 0 days.

(21) Appl. No.: 09/851,345

(22) Filed: May 9, 2001

(51) Int. Cl.$^7$ .............................................. G01N 23/00
(52) U.S. Cl. ............................................ 378/15; 378/15
(58) Field of Search .................................. 378/4–20

(56) References Cited

U.S. PATENT DOCUMENTS

| | | | |
|---|---|---|---|
| 4,618,789 A | 10/1986 | Flisikowski | 310/13 |
| 5,012,505 A | 4/1991 | Zupancic et al. | 378/130 |
| 5,628,918 A | 5/1997 | Mastalski | 216/8 |
| 6,276,145 B1 * | 8/2001 | Sharpless et al. | 378/15 |

* cited by examiner

*Primary Examiner*—Craig E. Church
(74) *Attorney, Agent, or Firm*—Fay, Sharpe, Fagan, Minnich & McKee, LLP

(57) ABSTRACT

A CT scanner (10) for obtaining a medical diagnostic image of a subject includes a stationary gantry (12), and a rotating gantry (14) rotatably supported on the stationary gantry (12) for rotation about the subject. A fluid bearing is interposed between the stationary gantry (12) and the rotating gantry (14) by means of radial and axial fluid bearing pads, (100) and (102) respectively. The fluid bearing provides a fluid barrier which separates the rotating gantry (14) from the stationary gantry (12). In a preferred embodiment, the fluid bearing provides for quieter CT scanner operation at high rotational speeds. Moreover, eliminating the physical contact between the gantries minimizes wear and optimizes longevity.

20 Claims, 5 Drawing Sheets

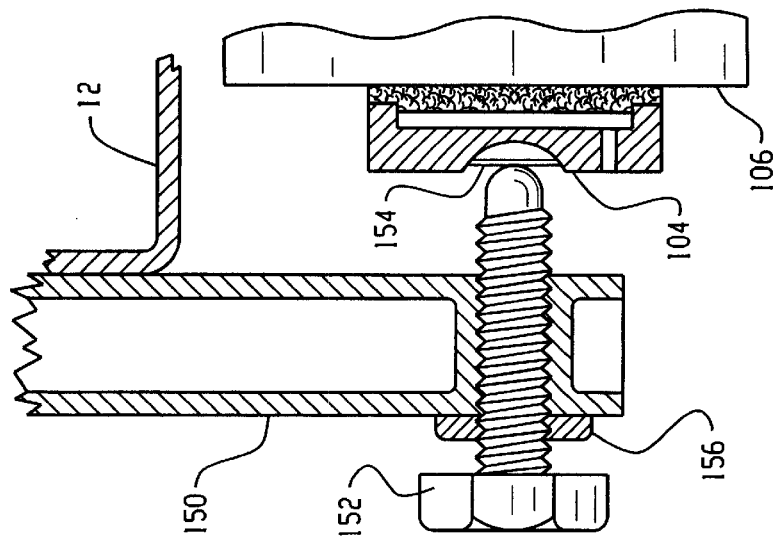
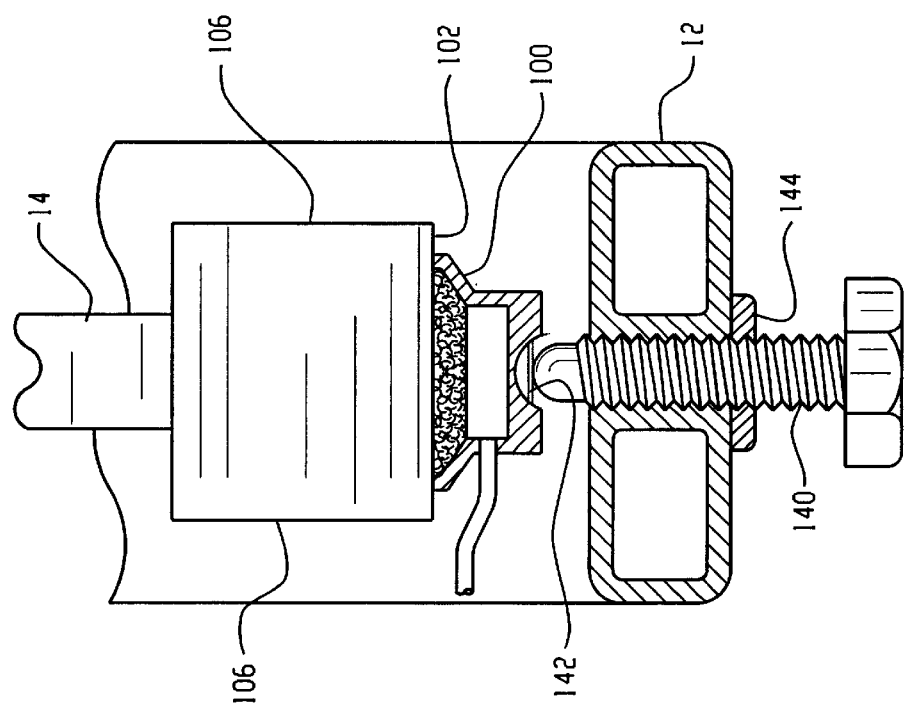
Fig. 5B
Fig. 5A

AEROSTATIC ROTOR BEARING

BACKGROUND OF THE INVENTION

The present invention relates to the art of medical diagnostic imaging. It finds particular application in conjunction with computed tomography (CT) scanners, and will be described with particular reference thereto. However, it is to be appreciated that the present invention is also amenable to other rotating gantry applications.

Generally, CT scanners have a defined examination region or scan circle in which a patient, or subject being imaged is disposed. A thin fan beam of radiation is transmitted across the examination region from an radiation source, such as an x-ray tube, to an oppositely disposed array of radiation detectors. The x-ray tube and associated power supply and cooling components are rotated around the examination region while data is collected from the radiation detectors. Rotation of the radiation source is often achieved by mounting the radiation source to a rotating gantry which is rotated on a stationary gantry.

The sampled data is typically manipulated via appropriate reconstruction processors to generate an image representation of the subject which is displayed in a human-viewable form. Various hardware geometries have been utilized in this process. In third generation scanners, both the source and detectors rotate around the subject. In a fourth generation scanner, the x-ray source rotates and the detectors remain stationary. The detector array typically extends 360° around the subject in a ring outside of the trajectory of the x-ray tube.

In previously developed CT scanners, commonly the rotating gantry is supported on the stationary gantry via a large diameter mechanical bearing including rolling elements or balls interposed between two raceways. The bearing was typically on the order of three quarters of a meter to two meters in diameter. Mechanical bearings typically have a small amount of play or clearance between the races and the rotating elements. The mechanical play permits the x-ray tube and detectors in a third generation scanner to move axially and radially and permits the plane of rotation to cant. Accurate reconstruction, typically to a resolution on the order of millimeters is dependant upon acquiring data from accurately resolved positions of the source and the detectors.

In helical volume scanning, CT fluoroscopy or other real time imaging techniques, and high speed imaging, the x-ray tube gantry rotates continuously at high speed. However, with increased rotational speed of the rotating gantry, noise levels associated with mechanical bearings reach unacceptable levels. In continuously rotating systems, friction related heating can restrict the length of scans. Moreover, the accompanying fiction causes wearing of parts in physical contact with one another thereby incurring increased play and noise, disadvantageous maintenance requirements, and a limited lifetime.

The present invention contemplates a new and improved gantry suspension technique which overcomes the above-referenced problems and others.

SUMMARY OF THE INVENTION

In accordance with one aspect of the present invention, a diagnostic imaging apparatus is provided. An x-ray source is mounted on a rotating gantry. The rotating gantry or a stationary gantry includes at least one smooth, annular bearing race. Fluid bearing pads are mounted to the other of the gantries, having a porous face that contacts the smooth annular bearing race. A pump supplies a bearing fluid to the pads to be ejected therefrom.

In accordance with another aspect of the present invention, A diagnostic imaging apparatus is provided. A plurality of individual bearing pads are mounted to a stationary gantry, at least some of them being mounted for individual radial adjustment. A rotating gantry including at least one bearing race is separated from the bearing pads by a thin layer of air as it rotates. An x-ray tube is mounted on the rotating gantry.

In accordance with another aspect of the present invention, a method of diagnostic imaging is provided. A rotating gantry is rotated about an imaging region. Fluid bearings are created between the rotating gantry and a plurality of fluid bearing pads. A bias of at least some of the bearing pads is adjusted. An image representation of a subject in an imaging region is reconstructed by irradiating the subject and reconstructing detected radiation.

One advantage of the present invention is faster CT tri scanner speeds and correspondingly reduced scan times.

Another advantage of the present invention is quieter CT scanner operation.

Another advantage of the present invention is extended bearing life with reduced maintenance.

Another advantage resides in a CT scanner with a larger gantry and bore.

Yet another advantage resides in the simplicity of the support structure.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 5A is detail view of a radial bearing pad support, in accordance with aspects of the present invention;

FIG. 5B is a detail view of an axial bearing pad support, in accordance with aspects of the present invention;

DETAILED DESCRIPTION OF THE PREFERRED EMBODIMENTS

Figure 1:
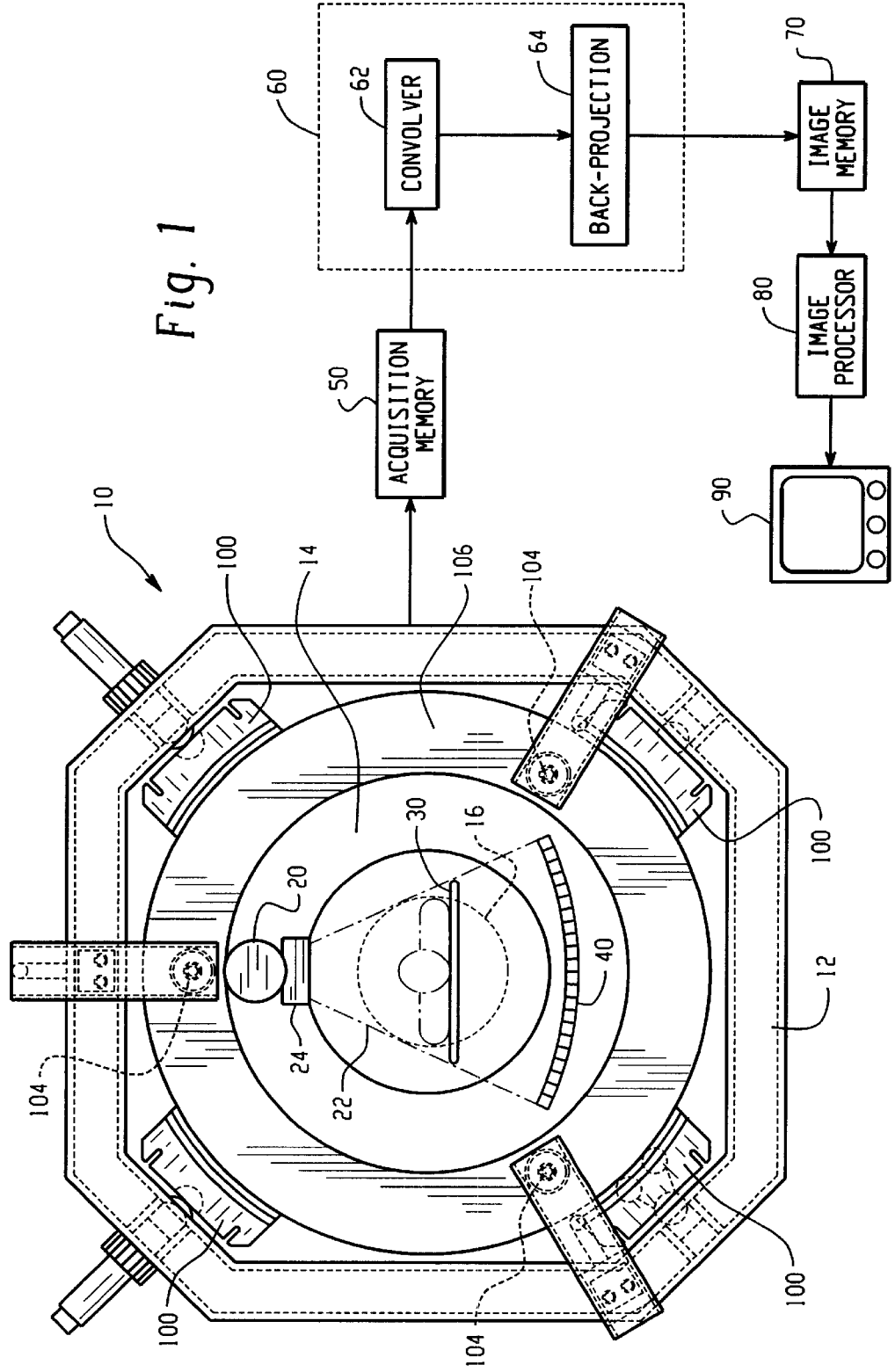
FIG. 1 is a diagrammatic illustration of a CT scanner in accordance with aspects of the present invention.

With reference to FIG. 1, a CT scanner 10 includes a stationary gantry 12 and a rotating gantry 14 which define an examination region 16. The rotating gantry 14 is suspended from the stationary gantry 12 for rotation about the examination region 16. A radiation source 20, such as an x-ray tube, is arranged on the main rotor 16 for rotation therewith. The radiation source 20 produces a beam of penetrating radiation 22 that passes through the examination region 16 as the rotating gantry 16 is rotated by an external motor (not illustrated) about a longitudinal axis of the examination region 16. A collimator and shutter assembly 24 forms the beam of penetrating radiation 22 into a thin fan shape and selectively gates the beam 22 on and off. Alternately, the radiation beam 22 is gated on and off electronically at the source 20. In any event, a subject support 30, such as a couch or the like, suspends or otherwise holds a subject being examined or imaged at least partially within the examination region 16 such that the fan-shaped beam of radiation 22 cuts a cross-sectional slice through the region of interest of the subject.

Optionally, the subject is successively repositioned such that neighboring cross-sectional slices are taken in consecutive indexed fashion to produce a three-dimensional volume of slices. Alternately, as is the case with continuous helical CT, concurrently with the rotation of the rotating gantry 14, the support 30, and consequently the subject thereon, are translated along a central horizontal axis of the examination region 16. In this manner, the source 20 follows a helical path relative to the subject.

In the illustrated third generation CT scanner, an array of radiation detectors 40 is mounted peripherally across from the source on the rotating gantry. Alternately, a fourth generation CT scanner is employed with a stationary ring of radiation detectors (not shown) mounted on the stationary gantry 12. Regardless of the configuration, the radiation detectors are arranged to receive the radiation emitted from the source 20 after it has traversed the examination region 14.

The radiation detectors 40 convert the detected radiation into electronic projection data. That is, each of the radiation detectors 40 produces an output signal which is proportional to an intensity of received radiation. Each radiation detector 40 generates data elements which correspond to projections along a corresponding ray within the view. Each element of data in a projection or data line is related to a line integral taken along its corresponding ray passing through the subject being reconstructed.

With source view geometry, as is typical with third generation scanners, each view or data line represents a fan of rays having an apex at the source 20 collected by concurrent sampling of all the radiation detectors 40 spanning the fan of radiation.

An acquisition memory 50 receives the sampled data from the radiation detectors 40. The acquisition memory 50 optionally performs filtering or other operations before passing the data to a reconstruction processor 60 which reconstructs image representations of the subject.

The reconstruction processor 60 processes the data from the acquisition memory board 50 and backprojects it into an image memory 70. The reconstruction processor 60 of the preferred embodiment includes a convolver 62 which convolves the data lines and a backprojector 64 which backprojects each convolved data line into the image memory 70. An image processor 80 selectively retrieves slices, projections, three-dimensional (3D) renderings, and other image information from the image memory 70 and appropriately formats an image representation for depiction on a human viewable display 90, such as a video monitor, CCD display, active matrix display, or the like.

Figure 2:
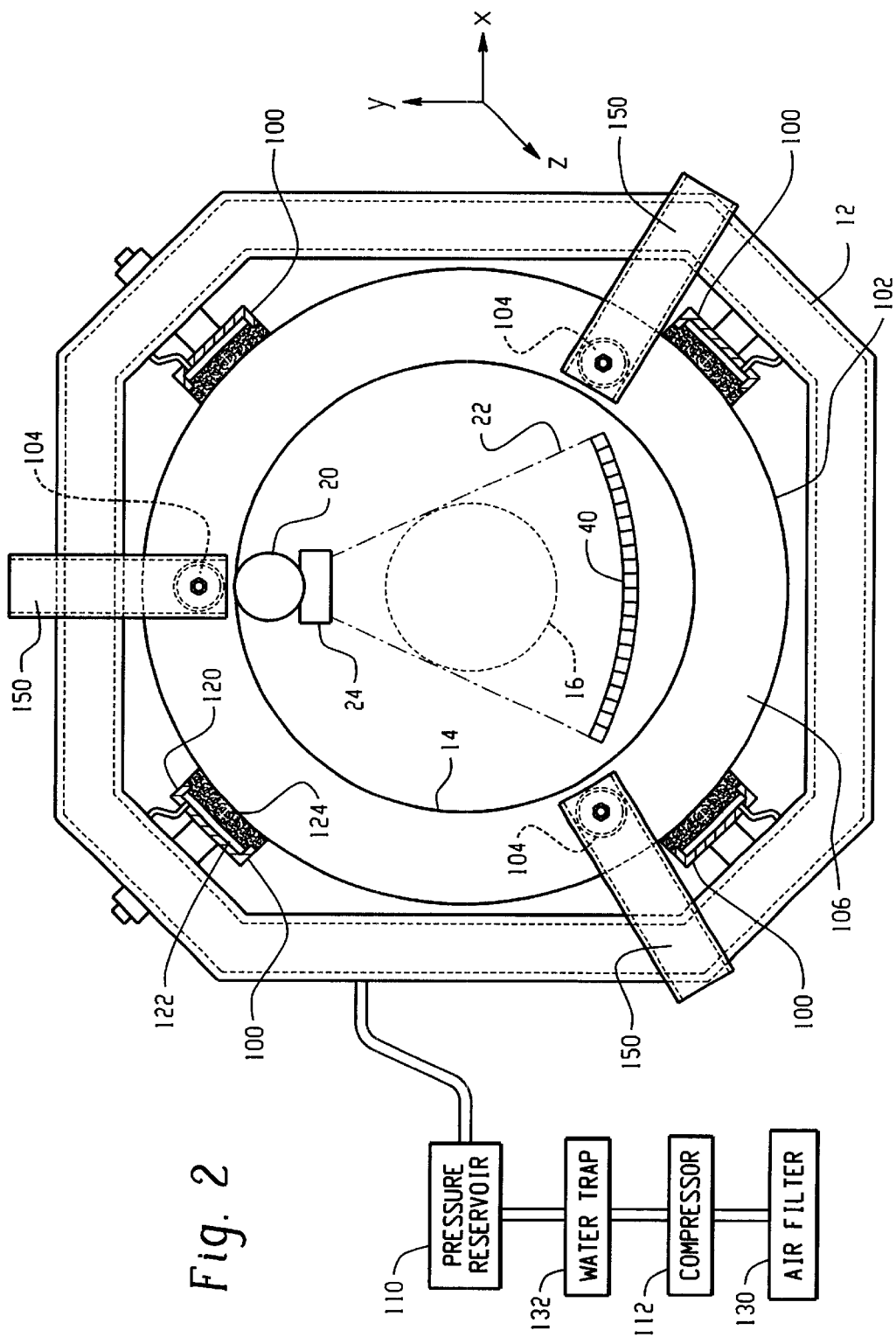
FIG. 2 is a frontal view of a main rotor and gantry support structure, in accordance with aspects of the present invention.

With reference to FIG. 2, the rotating gantry 14 is suspended from the stationary gantry 12 by a plurality of fluid bearing pads. In the preferred embodiment, two distinct types of bearing pads are utilized. Radial pads 100 contact the outer polished circumferential bearing surface or race 102 of the rotating gantry. Axial pads 104 contact proximal and distal flat circumferential faces or races 106 of the rotating gantry 14. A supply manifold supplies fluid to the bearing pads 100, 104 from a pressure reservoir 110. Fluid from the reservoir 110 is used to create fluid bearings between the pads 100, 104 and the races 102, 106, thereby effectively levitating the rotating gantry on micro-thin cushions of fluid. In the preferred embodiment, the fluid is air. Fluids, such as water and oil, are also contemplated. Preferably the reservoir 110 is kept at about 400 kPa, by a fluid compressor 112. The air bearing layers of the preferred embodiment are approximately 0.5 mm thick. The air bearings of the preferred embodiment provides a near-frictionless surface for the main rotor on which to rotate.

In the preferred embodiment, the air bearings each have a metal housing 120 that defines an air distribution passage 122 connected with the pressure manifold and the pressure reservoir 110. A porous pad 124 permits air to escape at a rate which maintains a fluid layer of about 0.5 mm between the porous pad and the race 102 (106). In order to minimize the possibility of introducing particles into the system (such as dust, dirt, etc.) that may degrade the bearing pads 124, air taken in to the compressor is first filtered by an air filter 130. A common problem with air compressors is that moisture in the air tends to condense when the air is compressed. In order to minimize the moisture introduced into the bearing system, an air line water trap 132 dehumidifies the compressed air.

In the event of power loss to the system while in operation, the reservoir 110 provides a sufficient buffer to sustain the bearings for a sufficient duration to decelerate the rotating gantry 14. This feature helps to make the system less susceptible to power outages, extending the life of the bearing pads.

In the preferred embodiment, four radial pads 100 contact the main rotor on its outer circumferential surface 102. These four bearing pads 100 keep the rotating gantry 14 stationary in x and y-directions, as illustrated in FIG. 2. Given an arbitrary load force, the bearings actively respond to counteract the load. A force that pushes the rotating gantry 14 against one or more pads causes the air gap between the race 102 and that pad 100 to narrow. As the thickness of the bearing decreases, the pressure increases, stiffening the bearing and counteracting the load force. Similarly, the bearings located on the rotor opposite the direction of the load force increase in thickness, decreasing their pressure. Thus, load forces tend to be canceled by the bearings.

Typical load forces also include the weight of the rotating gantry 14 including the x-ray tube, its power supply, its cooling system, detectors, and the like. Since this load force is always present, it has been contemplated to asymmetrically distribute the air bearing between radial pads 100. Optionally, more bearing fluid or higher bearing pressure can be supplied to the lower two radial bearing pads 100 to counteract the force of gravity.

Figure 3:
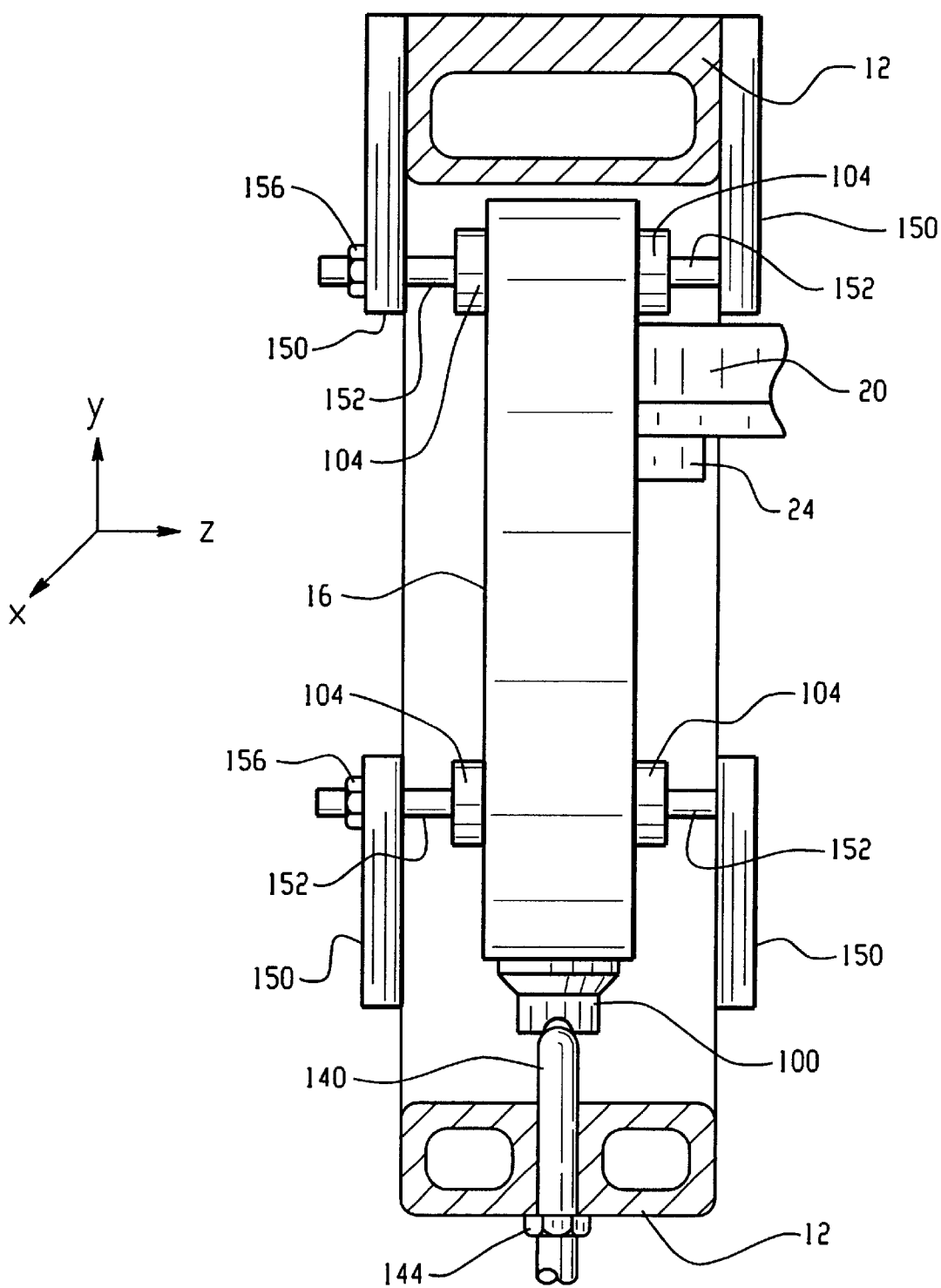
FIG. 3 is a side view of the main rotor and gantry support.

Similar to the radial bearing pads 100, the axial bearing pads 104 cancel forces in the z-direction, as illustrated in FIGS. 2 and 3. Longitudinal and canting displacements of the rotating gantry apply pressure in the z-direction to one or more of the axial bearing pads 104. As a result, the corresponding bearing is compressed, increasing its pressure, counteracting the displacement force. By virtue of the preferred arrangement of bearing pads 100, 104, load forces applied to the rotating gantry 14 are counteracted by one or more of the fluid bearings. Opposing pressures of the bearings induced by such displacement return the rotating gantry 14 to positional equilibrium in its original position.

Figure 4:
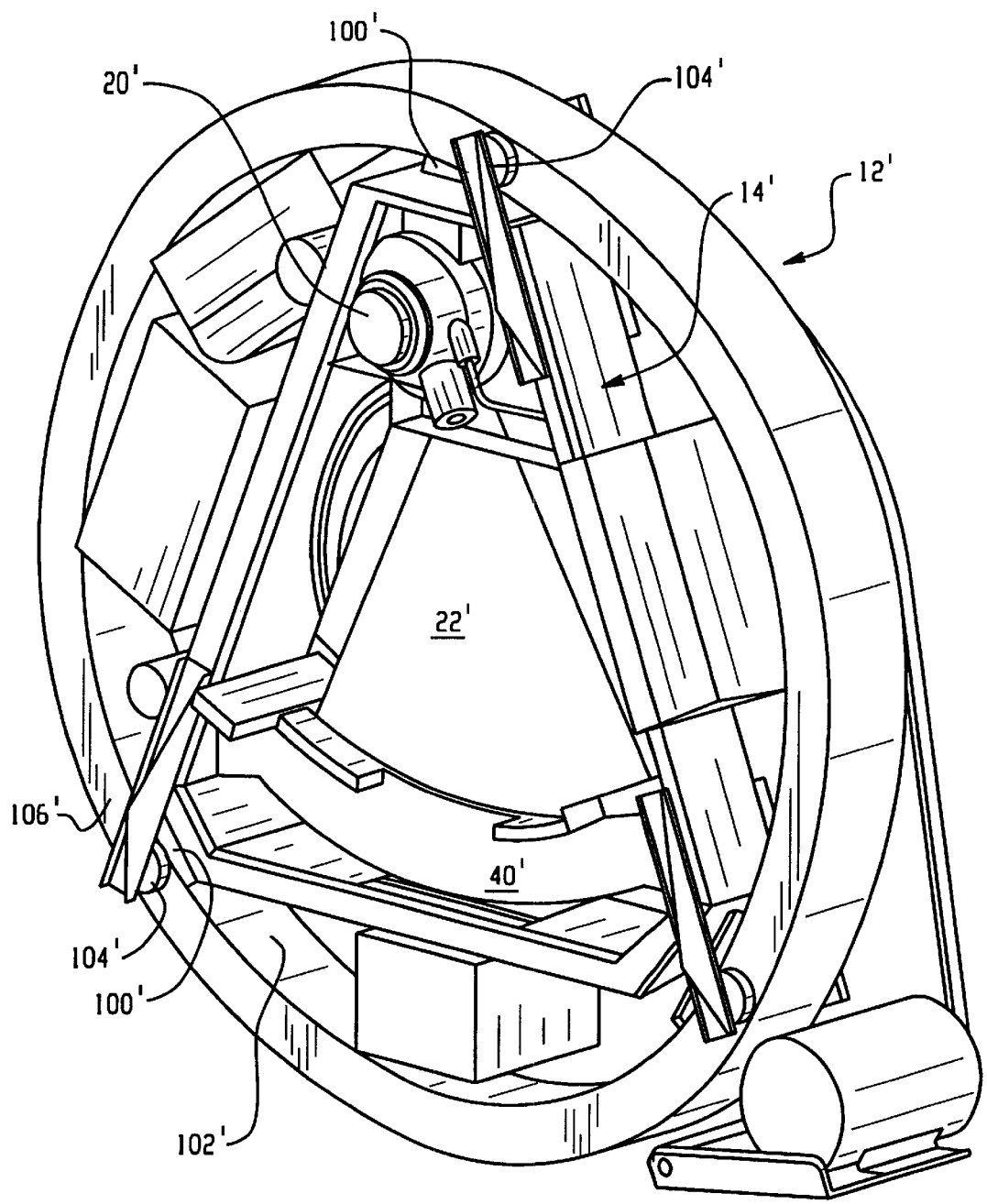
FIG. 4 is an alternate embodiment of the CT scanner gantry and rotor.

The bearing pads 100, 104 are not necessarily stationary. In an alternate embodiment as illustrated in FIG. 4, the bearing pads 100', 104' are attached to a rotating gantry 14' and rotate therewith. A stationary gantry 12' of this alternate embodiment supports an inner race 102' and oppositely disposed longitudinal races 106'. The radial pads 100' form fluid bearings with the inner circumferential race 102' and the axial pads 104' form bearings along the side races 106'.

With reference to FIG. 5A, and continuing reference to FIGS. 2 and 3, the radial bearing pads 100 are fixed with radial fixture assemblies, illustrated in detail in FIG. 5A. A radial pad 100 is secured to the stationary gantry 12 with a radial ball stud 140. Between an interface of the radial pad 100 and the radial ball stud 140 is a spring element, such as a Belville washer 142. The Belville washer 142 is flexible, has a selected, fixed spring constant in the preferred embodiment. During machine setup, the radial pads 100 are positioned adjacent the rotating gantry race 102 in an original configuration. The radial pads 100 are held in position by the radial ball studs 110. The studs are tightened to a desired tension and locked with a preload lock nut 144. Setup of the radial pads 100 determines the stiffness of the bearings in relation to the rotating gantry 14, defining the operating characteristics of the fluid bearings. The bearing stiffness is at least $3.5 \times 10^9$ Pa with $7.0 \times 10^9$ Pa being preferred Alternately, the Belville washer can be eliminated and the torque applied to the ball stud controlled precisely. As another alternative, other spring biasing mechanisms are contemplated, such as torsion springs, coil springs, fluid springs, and the like.

In the preferred embodiment, two of the four radial pads 100 are fitted with Belville washers or other still springs as discussed above. The remaining two pads 100 are supported in a fixed position without springs.

With continuing reference to FIGS. 2 and 3, the axial bearing pads 104 are fixed with axial fixture assemblies, as illustrated in detail in FIG. 5B. Each axial pad 104 is secured to a support arm 150 with an axial ball stud 152. A Belville washer 154 is disposed between an interface of the axial pad 104 and the axial ball stud 152. The Belville washer 154 is similar to the washers used in the radial support assembly. Again, other springs and pressure controlling devices are contemplated. During machine setup, the axial pads 104 are positioned adjacent the races 106. The axial pads 104 on one side are moved by the axial ball studs 152 without Belville washers to define the plane of rotation. The studs on the other side are tightened to the tension set by the Belville washers and secured with an axial preload lock nut 156. Setup of the axial pads 104 determines the original stiffness of the bearing in relation to the rotating gantry 14.

Optionally, load measuring sensors are included in each of the axial and radial support assemblies. Data gathered by such sensors is used to adjust bearing distribution to counteract load forces. Alternately, such data could be used as a quality control check by an operator, ensuring that the CT scanner is operating within tolerable load limits.

Numerous other devices in addition to the x-ray tube 20 and the detector array 40 are mounted on the rotating gantry 14. These include a coolant circulating system for the x-ray tube and high voltage generators for the x-ray tube. In order to minimize distortion of the rotating gantry 14, devices are mounted thereon such that their centers of gravity are in the plane of the scan beam 22 and their collective center of gravity is at the geometric center of the rotating gantry. As the rotating gantry 14 approaches high speeds (500–600 RPM) stresses of centripetal acceleration can distort the bearing races if components are not balanced adequately.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging apparatus comprising:

a rotating gantry;

an x-ray source mounted on the rotating gantry;

a stationary gantry;

at least one smooth, annular bearing race disposed on one of the rotating and stationary gantries;

a plurality of fluid bearing pads mounted to the other of the rotating and stationary gantries, each pad having a porous contact portion, the porous contact portion of each fluid bearing pad disposed contiguous to the bearing race;

a fluid pump for supplying a fluid to the fluid bearing pads, the fluid being ejected from the porous contact portions forming a rotating gantry supporting fluid layer between the bearing race and the bearing pads.

2. The diagnostic imaging apparatus as set forth in claim 1, wherein the x-ray producing apparatus includes:

a source from which x-rays emanate;

a coolant system that transfers heat away from the source into ambient surroundings.

3. The diagnostic imaging apparatus as set forth in claim 1, further including:

a reservoir containing the fluid used as the bearing fluid.

4. The diagnostic imaging apparatus as set forth in claim 1, further including:

a motor for rotating the rotating gantry about an imaging region.

5. The diagnostic imaging apparatus as set forth in claim 1, wherein the fluid is a gas.

6. The diagnostic imaging apparatus as set forth in claim 5, wherein the fluid is air.

7. The diagnostic imaging apparatus as set forth in claim 1, wherein the fluid bearing pads are attached to the outer gantry with pressure controlling means.

8. The diagnostic imaging apparatus as set forth in claim 7, wherein the pressure controlling means includes a Belville washer.

9. The diagnostic imaging apparatus as set forth in claim 1, wherein the at least one bearing race includes:

an outer annular bearing surface;

first and second parallel surfaces with a common central axis to each other and the outer bearing surface.

10. The diagnostic imaging apparatus as set forth in claim 9, wherein at least the outer annular bearing surface, the first parallel bearing surface, and the second parallel bearing surface are machined to be smooth.

11. The diagnostic imaging apparatus as set forth in claim 9, wherein the plurality of fluid bearing pads include a first portion of pads that are curved to conform to the outer annular bearing surface.

12. The diagnostic imaging apparatus as set forth in claim 11, wherein the fluid bearing pads include a second portion of pads whose porous contact portions are flat to conform to the parallel bearing surfaces.

13. The diagnostic imaging apparatus as set forth in claim 12, wherein the first portion of pads includes four pads, and the second portion of pads includes six pads.

14. A diagnostic imaging apparatus comprising:
a stationary gantry;
a plurality of individual bearing pads mounted to the stationary gantry, at least some of the bearing pads being mounted for individual radial adjustment;
a rotating gantry having at least one annular bearing race, the bearing race being disposed closely adjacent the bearing pads and separated therefrom by a thin layer of air as the rotating gantry rotates relative to the stationary gantry;
an x-ray tube mounted on the rotating gantry.

15. The diagnostic imaging apparatus as set forth in claim 14, wherein each individual bearing pad includes:
a housing having a pressurized air inlet and an air distribution passage;
an air permeable face facing the bearing race and in fluid communication with the air distribution passage, such that air passing through the air permeable face establishes the thin air layer between the air permeable face and the bearing race.

16. The diagnostic imaging apparatus as set forth in claim 15, wherein the at least one bearing race includes:
a pair of concentric annular races facing toward opposite sides of the rotating gantry, a plurality of the bearing pads being disposed closely adjacent each of the pair of races.

17. The diagnostic imaging apparatus as set forth in claim 15, further including:
a biasing means for biasing at least some of the pads toward the bearing race with a force of at least $3.5 \times 10^9$ Pa.

18. A method of diagnostic imaging comprising:
rotating a rotating gantry about an imaging region;
creating fluid bearings between the rotating gantry and a plurality of fluid bearing pads by pumping a fluid to a fluid reservoir, to the bearing pads, and ejecting the fluid from the bearing pads;
adjusting a bias on at least some of the bearing pads;
creating an image representation of a subject in the imaging region by irradiating the subject and reconstructing detected radiation.

19. The method as set forth in claim 18, further including:
maintaining a constant pressure in the fluid reservoir.

20. The method as set forth in claim 19, further including:
depleting the reservoir to sustain a bearing stiffness in an event of an air supply failure while the rotating gantry decelerates.

* * * * *